(12) United States Patent
Keller

(10) Patent No.: US 9,040,582 B2
(45) Date of Patent: May 26, 2015

(54) FORMULATION AND METHOD TO INDUCE A DEEP STATE OF RELAXATION

(76) Inventor: Raymond M. Keller, Bonita Springs, FL (US)

( * ) Notice: Subject to any disclaimer, the term of this patent is extended or adjusted under 35 U.S.C. 154(b) by 438 days.

(21) Appl. No.: 13/464,425

(22) Filed: May 4, 2012

(65) Prior Publication Data

US 2013/0210758 A1  Aug. 15, 2013

Related U.S. Application Data

(60) Provisional application No. 61/482,278, filed on May 4, 2011.

(51) Int. Cl.
*C07C 229/36* (2006.01)
*C07D 209/16* (2006.01)
*C07D 209/20* (2006.01)

(52) U.S. Cl.
CPC ............ *C07C 229/36* (2013.01); *C07D 209/20* (2013.01); *C07D 209/16* (2013.01)

(58) Field of Classification Search
None
See application file for complete search history.

(56) References Cited

U.S. PATENT DOCUMENTS

| | | | |
|---|---|---|---|
| 4,664,927 A * | 5/1987 | Finkel | 426/330 |
| 4,900,566 A | 2/1990 | Howard | |
| 5,612,074 A | 3/1997 | Leach | |
| 6,503,543 B1 | 1/2003 | Hudson et al. | |
| 6,656,473 B2 | 12/2003 | Hudson et al. | |
| 6,866,874 B2 | 3/2005 | Hudson et al. | |
| 7,048,941 B2 | 5/2006 | Altaffer et al. | |
| 7,223,417 B2 | 5/2007 | Calton et al. | |
| 2006/0083700 A1 * | 4/2006 | Cherukuri et al. | 424/59 |
| 2006/0281691 A1 * | 12/2006 | Blass | 514/23 |
| 2007/0172570 A1 * | 7/2007 | DeBrock et al. | 426/594 |

FOREIGN PATENT DOCUMENTS

GB  2370504  *  8/2000  ............. A61K 49/00

OTHER PUBLICATIONS

Russell, A.D., "Mechanisms of bacterial resistance to non-antibiotics: food additives and food and pharmaceutical preservatives" Journal of Applied Bacteriology (199) vol. 71 pp. 191-201.*

* cited by examiner

*Primary Examiner* — Eric Olson
(74) *Attorney, Agent, or Firm* — Malloy & Malloy, P.L.

(57) ABSTRACT

A relaxation formulation structured to induce a deep state of relaxation in a person comprises amounts of tryptophan, melatonin, vitamin B3, and vitamin B6. Another relaxation formulation also includes an amount of tyrosine, and yet another formulation includes an amount of vitamin B12. At least one embodiment of a relaxation formula comprises a physiologically effective amount of gamma-aminobutyric acid ("GABA"). A delivery system is provided to facilitate administration of the relaxation formulation to a person. The delivery system may include an edible high carbohydrate matrix, such as a chocolate brownie. Alternatively, the delivery system may comprise an inert vaporizable compound to allow the components of the relaxation formulation to be inhaled directly into the lungs of a person. Other delivery systems include an aqueous sublingual spray and a beverage.

5 Claims, No Drawings

FORMULATION AND METHOD TO INDUCE A DEEP STATE OF RELAXATION

CLAIM OF PRIORITY

The present application is based on and a claim of priority is made under 35 U.S.C. Section 119(e) to the provisional patent application that is currently pending in the U.S. Patent and Trademark Office having Ser. No. 61/482,278 and a filing date of May 4, 2011, and which is incorporated herein by reference in its entirety.

BACKGROUND OF THE INVENTION

1. Field of the Invention

The present invention is directed to a formulation specifically intended to induce a deep state of relaxation in a person consuming the same. An edible and appetizing delivery system may be provided, wherein the delivery system itself comprises additional and beneficial synergistic effects on the metabolism of the components of the relaxation formulation within the body. Further, a method of inducing a deep state of relaxation in a person is disclosed comprising at least the step of administering an amount of a relaxation formulation to the person.

2. Description of the Related Art

Serotonin is the common name for 5-hydroxytryptamine ("5-HT"), a monoamine neurotransmitter which is primarily found in the gastrointestinal tract, blood platelets, and the central nervous system of many animals, including human beings. Serotonin in the central nervous system is known to facilitate or increase communications between neurons allowing the central nervous system to function more effectively. It has been alleged that the effectiveness of the well known antidepressant Prozac® is due to an increase in the amount of serotonin in the synaptic gap which slightly separates individual nerve cells from one another, as a result of the drug. More in particular, serotonin has been shown to promote well being, calm, or relaxation in humans. Further, serotonin is believed to counter-balance the effects of dopamine and noradrenaline in the central nervous system, which are believed to promote arousal, fear, anger, and/or violent behavior, as well as other similarly undesirable emotions.

Tryptophan is an essential amino acid which is found in animal and vegetable protein based diets of many animals, once again, including human beings. Of the eight (8) essential amino acids and the fourteen (14) non-essential amino acids found in the foods of a normal diet, the amount of tryptophan present is the least of all. Despite its relative scarcity in the diet, the human body utilizes tryptophan for a variety of purposes. As one example, tryptophan is converted in the liver to form vitamin B3 in person's who are deficient in this essential compound. Furthermore, in person's who are even slightly deficient in vitamin B6, tryptophan may be metabolized into mildly toxic metabolites, such as hydroxykynurenine, xanthurenic acid and hydroxyanthranilic acid, within the body itself. As a result of these other processes which occur in the human body and compete for the limited amounts of tryptophan which a person obtains from their diet, it has been reported that the brain typically receives less than one (1) percent of the tryptophan present in a typical human diet.

The availability of tryptophan for conversion into serotonin in a person's brain is further limited by the blood brain barrier ("BBB"). While the BBB primarily serves to prevent toxins from entering the brain, it also serves to limit transport of amino acids, such as tryptophan, into the brain. Further exacerbating the problem is that tryptophan must complete with at least five (5) other amino acids for transport across the BBB into the brain, so as to be available for conversion into serotonin. It has been reported that the other competing amino acids may be present in amounts which are eight times the amount of tryptophan. It is also noteworthy that serotonin itself is not transported across the BBB, thus, the only serotonin available for use by the brain must be produced internally or converted from tryptophan, or its intermediate, which have crossed the BBB.

One approach which has been put forth to increase the amount of tryptophan available for transport across the BBB and conversion into serotonin in the brain is simply to provide a person with a high protein diet, thereby increasing the total amount of tryptophan ingested by the person. Unfortunately, this approach also results in proportionally increasing the amounts of other essential and non-essential amino acids which are present in the food source in the person's body. As noted above, tryptophan is the least concentrated amino acid found in most food products, and further, the tryptophan present in the food source must compete with many other amino acids present in the food for transport across the BBB. Thus, simply increasing a person's intake of tryptophan via food sources also results in an increase in other amino acids in the person's body which compete for transport across the BBB. As such, this approach, at best, only minimally increases the amount of tryptophan which ultimately crosses the BBB for conversion into serotonin.

An alternative dietary strategy is to provide a person with a high carbohydrate diet, which results in the body producing increased amounts of insulin to metabolize the additional carbohydrates to prevent elevated blood sugar levels. It has been noted that the insulin has the further effect of clearing a significant amount of amino acids present in the food source from the person's blood stream, thereby significantly minimizing the competition for the transport of tryptophan across the BBB for ultimate conversion into serotonin. Of course, this approach has a significant drawback in that the metabolism of the carbohydrates and competing amino acids from the person's blood stream by the insulin is ultimately stored as body fat.

Yet another alternative approach for increasing the availability of tryptophan for conversion into serotonin in the brain is simply to provide a person with a supplement of essentially pure tryptophan, thereby eliminating the problem of corresponding increases in the concentration of competing amino acids which are present in the person's diet. It has been shown, however, that elevated levels of tryptophan in a person's blood stream can elevate the production of an enzyme known as tryptophan pyrolase ("TP") in the liver, which breaks down tryptophan in the body before it is able to cross the BBB. TP production is also known to be activated by the hormone cortisol which is produced in the adrenal glands when a person is under stress. Thus, a person under stress attempting to achieve a state of relaxation by taking a tryptophan supplement is actually at risk of elevated production of TP in the liver, which subsequently metabolizes the tryptophan in the blood stream before it reaches the brain for the production of serotonin. Vitamin B3 is known to inhibit TP production in the liver. Furthermore, vitamin B3 is known to activate the enzyme that converts tryptophan to 5-hydroxytryptophan ("5-HTP"), which is a precursor or intermediate between tryptophan and serotonin. In addition, vitamin B6 is known to activate the carboxylase enzyme which then converts 5-HTP to serotonin.

Just as tryptophan is a precursor for serotonin production, tyrosine is a precursor to the production of both dopamine and noradrenaline. The enzyme that converts tyrosine to dopamine or noradrenaline is tyrosine hydroxylase which has been found to be at least twenty-five (25) percent unsaturated in many persons. Thus, supplemental dosages of tyrosine may result in increased levels of dopamine and/or noradrenaline in a person's bloodstream, which may trigger the body to produce greater amounts of serotonin as a balance.

Melatonin is another naturally occurring compound found in many plants and animals. In particular, in human beings, melatonin is secreted into the blood by the pineal gland of the brain. More in particular, the pineal gland converts serotonin into melatonin. Melatonin supplements have been available as a sleep aid and for the treatment of certain types of insomnia. Melatonin is also believed to reduce the levels of cortisol in a person's bloodstream, and as noted above, cortisol is known to activate the liver's production of TP, an enzyme which degrades tryptophan before it is able to cross the BBB for conversion into serotonin.

Gamma-aminobutyric acid ("GABA") is the main inhibitory neurotransmitter in the central nervous system of human beings. GABA reportedly helps reduce mental and physical stress when a person is in an over-excited state. Foods high in glutamine or theanine are believed to enhance the production of GABA in the brain. Research has shown that chocolate enhanced with GABA produced physiological stress-reducing effects, increased relaxation and immunity, while reducing anxiety in test subjects.

Therefore, it would be beneficial to provide a relaxation formulation which maximizes the amount of tryptophan available for transport across the BBB for subsequent conversion into serotonin in the brain. It would be desirable for such a relaxation formulation to incorporate components which further facilitate the conversion of tryptophan to 5-HTP and subsequent conversion to serotonin within a person's brain. It would be further helpful to provide a relaxation formulation incorporating components which inhibit metabolism of tryptophan in the person's body before it crosses the BBB, for example, inhibiting the conversion of tryptophan by TP in the liver. Another benefit may be realized by incorporating a physiologically effective amount of gamma-aminobutyric acid ("GABA") into a relaxation formula to enhance the relaxing and stress reducing effects of the formulation experienced by a user. It would also be preferable to provide a relaxation formulation comprised solely from components which are deemed GRAS, i.e., generally recognized as safe, by the Food and Drug Administration ("FDA"), so as to minimize or eliminate FDA regulation of the same.

A further benefit would be realized by providing a delivery system for such a formulation which serves to reduce competing amino acids in a person's bloodstream so as to further facilitate the transport of tryptophan across the BBB into the person's brain for conversion into serotonin. It would also be helpful to provide a delivery system which in and of itself serves to synergistically enhance the beneficial effects of the tryptophan present in a relaxation formulation. Yet a further benefit may be realized by providing a relaxation formulation which may be vaporized for inhalation by a person in order to enhance and expedite the onset of a deep state of relaxation resulting therefrom.

SUMMARY OF THE INVENTION

The inventive formulation of the present invention is specifically derived to enhance the beneficial synergistic effects of tryptophan in combination with the additional components disclosed and described hereinafter, in order to maximize the transport of tryptophan across the blood brain barrier ("BBB") where it is available for production of serotonin for the person's brain.

At least one embodiment of a relaxation formulation structured to induce a deep state of relaxation in a person in accordance with the present invention comprises amounts of tryptophan, tyrosine, melatonin, and at least one vitamin selected from the group consisting of vitamin B3, vitamin B6, and vitamin B12. More in particular, a unit dosage of one embodiment of the relaxation formulation of the present invention comprises an amount of L-tryptophan in a range of about 250 to 3,000 milligrams, an amount of tyrosine in a range of about 25 to 300 milligrams, an amount of melatonin in a range of about 1 to 10 milligrams, an amount of vitamin B3 in a range of about 3 to 36 milligrams, an amount of vitamin B6 in a range of about 5 to 75 milligrams, and an amount of vitamin B12 in a range of about 1 to 10 micrograms.

Yet another embodiment of the present relaxation formulation comprises an amount of L-tryptophan of about 2,000 milligrams, an amount of melatonin of about 3 milligrams, an amount of vitamin B3 of about 12 milligrams, an amount of vitamin B6 of about 25 milligrams, and an amount of vitamin B12 of about 3 micrograms.

At least one embodiment of the present relaxation formulation comprises a physiologically effective amount of gamma-aminobutyric acid ("GABA") in the range of between about 1 to 5 milligrams/milliliter ("mg/ml"), depending on the delivery system employed for the relaxation formula.

The present invention further comprises a delivery system for the inventive relaxation formulation. More in particular, in at least one embodiment, the delivery system may comprise an edible food product, for example, a chocolate brownie. A chocolate brownie, or other high carbohydrate food matrix, will trigger the production of insulin upon ingestion by a person, which will aid in clearing the person's blood of amino acids which compete with tryptophan for transport across the blood brain barrier, thus allowing more tryptophan to enter the brain for conversion into serotonin and inducing the deep state of relaxation. In at least one further embodiment, the delivery system comprises an inert vaporizable compound, to allow the active components of the relaxation formulation of the present invention to be inhaled directly into the person's lungs.

The present invention further contemplates a method for inducing a deep state of relaxation in a person, wherein the method comprises the step of administering at least a portion of a unit dosage of a relaxation formulation to the person, wherein the relaxation formulation comprises predetermined amounts of each of tryptophan, melatonin, vitamin B3, and vitamin B6.

These and other objects, features and advantages of the present invention will become clearer when the detailed description is taken into consideration.

DETAILED DESCRIPTION

The present invention is directed to a formulation specifically developed to induce a deep state of relaxation upon administration of an appropriate dosage of the same to a person. More in particular, the formulation of the present invention will induce a deep state of relaxation in a person upon administering at least a portion of a unit dosage of the formulation as described in further detailed below. In at least one embodiment, the relaxation formulation of the present invention is administered to a person by way of a delivery system comprising of a carbohydrate based food product including, but in no manner limited to, a chocolate brownie. Another embodiment includes a delivery system for the present relaxation formulation in the form of a drink or beverage. The relaxation formulation of the present invention may also be provided in the form of a spray, such as, an aqueous sublingual spray which a person may administer directly under his or her tongue. In at least one further embodiment, the present inventive relaxation formulation is structured to be administered to a person in a vaporized form to be inhaled directly into the lungs of the person.

As noted above, the present relaxation formulation includes an amount of L-tryptophan in conjunction with one or more additional components specifically selected for beneficial synergistic affects on the metabolism of L-tryptophan in a person's body. In at least one embodiment, a unit dosage of the present relaxation formulation comprises an amount of L-tryptophan of approximately 1,000 milligrams ("mg"). In one further embodiment, a unit dosage of the present relaxation formulation includes an amount of L-tryptophan of about 2,000 mg. Of course, it is within the scope and intent of the present invention for a unit dosage of the relaxation formulation to comprise an amount of L-tryptophan in a range of from about 250 mg up to about 3,000 mg.

As noted above, in order to induce a deep state of relaxation in a person, at least a portion of a unit dosage of the present inventive relaxation formulation would be administered to a person. More in particular, although disclosed herein in terms of a "unit dosage" for ease of description, the actual amount of the present relaxation formulation required to induce a deep state of relaxation may vary considerably from person to person. As such, at least initially, a person may choose to consume only a fraction of a "unit dosage", for example, one-half, one-third, or even as little as one-quarter of a "unit dosage", in order to evaluate the effects on himself or herself. Additional portions may then be consumed in ten to fifteen minute intervals, until such time as the person has achieved a desired level of relaxation. Of course, subsequently, once a person knows his or her optimal dosage, he or she may consume that full amount at one time, which may still comprise only a portion of a "unit dosage", a full "unit dosage", or, perhaps, more than a single "unit dosage".

In addition to L-tryptophan, as noted above, in at least one embodiment the relaxation formulation of the present invention also comprises an amount of tyrosine, a precursor in the formation of dopamine and noradrenaline in the body. In at least one embodiment, the relaxation formulation of the present invention comprises tyrosine in an amount equal to about 10:1 L-tryptophan to tyrosine. More in particular, a unit dosage of at least one embodiment of the present relaxation formulation comprises about 1,000 mg of L-tryptophan and about 100 mg of tyrosine. Tyrosine has been included in the present inventive formulation as it is believed that the body will naturally tend to convert more L-tryptophan to serotonin in the brain when the levels of dopamine and/or noradrenaline are increased in the person's blood system. As such, administering an amount of tyrosine in a ratio of about 10:1 L-tryptophan to tyrosine will result in the production and release of additional dopamine and/or noradrenaline into the person's bloodstream, thereby causing the body to convert L-tryptophan to serotonin in the brain in attempts to offset the increased levels of dopamine and/or noradrenaline in the person's system.

Of course, the present relaxation formulation need not include tyrosine. More in particular, in at least one embodiment, a unit dosage of the present relaxation formulation comprises an amount of L-tryptophan of about 2,000 mg, without any tyrosine. In such an embodiment, the elevated amount of L-tryptophan in the unit dosage is believed sufficient to trigger the body's conversion of L-tryptophan to produce sufficient amounts of serotonin in the brain in order to induce a deep state of relaxation in the person.

In addition to L-tryptophan and tyrosine, at least one embodiment of the inventive formulation in the present invention also includes an amount of melatonin. Melatonin is produced in the pineal gland from serotonin, and as such, it is incorporated into the inventive relaxation formulation of the present invention to reduce activity in the pineal gland, thereby minimizing the metabolism of serotonin within the person's body. Further, as noted above, melatonin is believed to reduce the levels of cortisol in a person's bloodstream, thereby reducing the production of TP in the liver which, as also noted above, can metabolize L-tryptophan in the body before it is transported across the BBB. A result of the addition of melatonin to the present inventive formulation is believed to be an increased production of serotonin in the brain, and thus, an increased amount of serotonin available to induce a deep state of relaxation, which is the intended effect of the present formulation. In at least one embodiment, a unit dosage of the present inventive relaxation formulation comprises an amount of melatonin in the range of about 1 mg to about 10 mg. In at least one further embodiment, a unit dosage of the present formulation comprises an amount of melatonin of about 3 mg.

In addition to the aforementioned components, namely, L-tryptophan, tyrosine, and melatonin, the present inventive relaxation formulation includes amounts of one or more "B" vitamins including, but not limited to, vitamin B3, vitamin B6, and/or vitamin B12.

As previously noted, the body, and more specifically, the liver, metabolizes tryptophan by way of TP conversion in order to produce vitamin B3, in persons who are deficient in this essential compound. Thus, the incorporation of an amount of vitamin B3 in the present inventive formulation is believed to inhibit the metabolism of tryptophan in the liver by way of TP conversion, thus increasing the availability of tryptophan in the person's blood stream for transport across the BBB, for ultimate conversion into serotonin in the brain. In at least one embodiment, the present inventive formulation comprises vitamin B3 in an amount ranging from about 3 mg to about 36 mg. In one further embodiment, a unit dosage of the present inventive formulation comprises an amount of vitamin B3 in an amount of 12 mg.

In addition, it has been noted that tryptophan degrades in the bodies of persons who have deficient levels of vitamin B6 in their system. Furthermore, it has been observed that vitamin B6 aids in the conversion of 5-HTP, an intermediate in the metabolism of tryptophan to serotonin in the brain. As such, the present inventive formulation includes a synergistic amount of vitamin B6 in order to, first, increase the amount of tryptophan available for transport across the BBB, and, second, to facilitate the conversion of 5-HTP to serotonin in the person's brain. In at least one embodiment, the present inventive formulation comprises vitamin B3 in an amount ranging from about 5 mg to about 75 mg. In one further embodiment, a unit dosage of the present inventive relaxation formulation includes an amount of vitamin B6 in an amount of about 25 mg.

In one further embodiment, the inventive formulation of the present invention also comprises an amount of vitamin B12. Vitamin B12 is added to the inventive formulation in view of its known calming properties. A unit dosage of the inventive formulation of the present invention, in at least one embodiment, comprises an amount of vitamin B12 in a range of about 1 microgram ("μgm") to about 10 micrograms. In at least one further embodiment, a unit dosage of the present relaxation formulation comprises an amount of vitamin B12 in an amount of about 3 micrograms.

In at least one embodiment, the relaxation formulation of the present invention comprises a physiologically effective amount of gamma-aminobutyric acid ("GABA"). More in particular, in addition to one or more of the aforementioned components, a relaxation formulation in accordance with the present invention may comprise GABA in the range of between about 1 to 5 milligrams/milliliter ("mg/ml"), depending on the delivery system employed for the relaxation formula. As previously noted, research has indicated that GABA helps reduce mental and physical stress, and can enhance the feeling of relaxation in a user.

The present invention further envisions a number of delivery systems for the inventive relaxation formulation disclosed and described above. In at least one embodiment, the delivery system comprises an edible product to be ingested by a person. In yet one other embodiment, the delivery system comprises a pleasant tasting edible product for ingestion by a person, and in one further embodiment, the pleasant tasting edible food product comprises a high carbohydrate matrix. The provision of a high carbohydrate matrix delivery system will trigger insulin production in a person following ingestion. As noted above, insulin serves to clear the person's bloodstream of the amino acids which compete with tryptophan for transport across the blood brain barrier, thereby synergistically enhancing the amount of tryptophan transported across the BBB and converted to serotonin in the person's brain, thus, inducing a deep state of relaxation in the person.

One example of a pleasant tasting edible food product having a high carbohydrate content is a chocolate brownie. Of course, it is well within the scope and intent of the present invention for the delivery system to encompass any of a number of pleasant tasting baked goods including cookies, donuts, pastries, etc. Further, a high carbohydrate content food spread, such as peanut butter, hazelnut spread, etc., could be employed as a delivery system within the scope and intent of the present invention. Further, a high carbohydrate liquid may also be employed as a delivery system, such as a milkshake, malt etc. Once again, it is well within the scope and intent of the present invention for any of as number other high carbohydrate food matrices to be employed as a delivery system in accordance with the present invention.

As one further example, in at least one embodiment, a unit dosage of the present inventive formulation comprises an amount of L-tryptophan of about 1,000 mg, tyrosine in an amount of about 100 mg, about 3 mg of melatonin, about 12 mg of vitamin B3, about 25 mg of vitamin B6, and about 3 μgm of vitamin B12, wherein each of the foregoing components is admixed into a chocolate brownie delivery system having a net weight of approximately 2 ounces, or 57 grams.

Yet another embodiment comprises an additional amount of L-tryptophan without any tyrosine. Specifically, a unit dosage of the present relaxation formulation in at least one embodiment comprises L-tryptophan in an amount of about 2,000 mg, about 3 mg of melatonin, vitamin B3 in an amount of about 12 mg, about 25 mg of vitamin B6, and about 3 μgm of vitamin B12, each of these components being admixed into a chocolate brownie having a net weight of approximately 2 ounces, or 57 grams.

The preparation of the aforementioned chocolate brownie delivery system is preferably conducted in a conventional rotating rack oven to ensure even heat distribution throughout the baking process. Further, the temperature to which the brownie mixture is subjected should not exceed 350° F., which is well below the flash point of the amino acids and vitamins of the present formulation, thereby preventing the formation of any pyrolysis byproducts in the delivery system. Under the aforementioned conditions, the baking time for the chocolate brownie delivery system is about 25 and 45 minutes at 350° F., and in at least one embodiment, the baking time is about 35 minutes at 350° F.

In at least one further embodiment, the delivery system comprises an uncooked chocolate brownie mix, to which a person adds water, eggs, and milk, and which the person may bake in a home oven at a temperature of no more than 350° F. for about 35 minutes. After baking, the person cuts the sheet of baked brownies into portions equal to about two (2) ounces each, wherein each portion will comprise about 1,000 mg of tryptophan, 100 mg of tyrosine, 25 mg of vitamin B3, 3 mg of vitamin B6, and 3 μgm of vitamin B12.

At least one further delivery system is envisioned wherein a unit dosage of the relaxation formation as disclosed herein is admixed with an inert carrier compound which is structured to be readily vaporized upon exposure to a heat source, such as, by way of example only, the heat source of a commercially available electronic cigarette. In this embodiment, a unit dosage, or a portion thereof, of the present relaxation formulation may be administered to the person in an manner which will cause almost instantaneous results, i.e., the person will almost immediately experience a deep state of relaxation upon inhalation of an amount of the present relaxation formulation via the presently disclosed vaporized delivery system.

Yet one further delivery system for the present relaxation formulation is an aqueous sublingual spray, which a person may administer directly under his or her tongue. In at least one embodiment, an amount of glycerin may be added to an aqueous sublingual spray delivery system in order to thicken the solution to provide a smoother mouth feel. Additionally, predetermined amounts of sugar and/or L-malic acid may be added to the aqueous sublingual spray delivery system to produce an acceptable balance of sweetness to tartness. In one embodiment, the sugar is either sucrose or fructose or some combination of both, and the sugar concentration may vary from 20 to 60 milligrams per milliliter ("mg/ml"), depending in part on the amount of L-malic acid present in the formulation.

Table 1 below is illustrative of one embodiment of the present relaxation formulation in an aqueous sublingual spray delivery system. Each of the components is dissolved into an amount of water to the appropriate concentrations indicated below. Of course, it is well within the scope and intent of the present invention for additional embodiments of an aqueous sublingual spray delivery system to be employed to administer the present relaxation formulation to a person.

TABLE 1

| Component | Concentration |
| --- | --- |
| Tryptophan | 5-15 mg/ml |
| Tyrosine | 1-1.5 mg/ml |
| Melatonin | 0.3-0.9 mg/ml |
| Vitamin B3 | 0.5-2.0 mg/ml |
| Vitamin B6 | 0.1-0.5 mg/ml |
| L-Malic Acid | 0.5-2.0 mg/ml |
| Sodium Benzoate | 0.5-1.5 mg/ml |
| Sugar | 20.0-60.0 mg/ml |

In at least one embodiment, the present relaxation formulation having approximately the following concentrations of components is incorporated into an aqueous sublingual spray delivery system: tryptophan—10.125 mg/ml; tyrosine—1.0125 mg/ml; melatonin—0.61 mg/ml; vitamin B3—1.35 mg/ml; vitamin B6—0.27 mg/ml; L-malic acid—1.62 mg/ml; sodium benzoate—1.0 mg/ml; and, sugar 37.0 mg/ml.

In yet one further embodiment, a flavor component may be added to an aqueous sublingual delivery system comprising the present relaxation formulation such as, by way of example only, the illustrative formulations presented above in Table 1. More in particular, Table 2 below is illustrative of just a few of the possible flavor components which may be added to the present inventive relaxation formulation for administration to a person via an aqueous sublingual spray delivery system.

TABLE 2

| Flavor Component | Concentration |
| --- | --- |
| Cherry | 5.0-15.0 mg/ml |
| Raspberry | 2.0-6.0 mg/ml |
| Apple | 5.0-15.0 mg/ml |
| Peppermint | 5.0-15.0 mg/ml |

Table 3 below is illustrative of an embodiment of the present relaxation formulation including GABA for use with an aqueous sublingual spray delivery system. Each of the components is dissolved into an amount of water to the appropriate concentrations indicated below. Once again, it is well within the scope and intent of the present invention for additional embodiments of an aqueous sublingual spray delivery system including GABA to be employed to administer the present relaxation formulation to a person.

TABLE 3

| Component | Concentration |
| --- | --- |
| Tryptophan | 5-15 mg/ml |
| Tyrosine | 0.5-1.5 mg/ml |
| Melatonin | 0.3-0.9 mg/ml |
| Vitamin B3 | 0.5-2.0 mg/ml |
| Vitamin B6 | 0.1-0.5 mg/ml |
| Gamma-aminobutyric acid | 1-5 mg/ml |
| L-Malic Acid | 0.5-2.0 mg/ml |
| Sodium Benzoate | 0.5-1.5 mg/ml |

In at least one embodiment, the present relaxation formulation having approximately the following concentrations of components is incorporated into an aqueous sublingual spray delivery system: tryptophan—10.125 mg/ml; tyrosine—1.0125 mg/ml; melatonin—0.61 mg/ml; vitamin B3—1.35 mg/ml; vitamin B6—0.27 mg/ml; gamma-aminobutyric acid ("GABA")—3.33 mg/ml; L-malic acid—1.62 mg/ml; and, sodium benzoate—1.0 mg/ml. As before, a flavor component may be incorporated into the foregoing exemplary relaxation formulation such as, for example, as disclosed above in Table 2.

Table 4 discloses an embodiment of the present relaxation formulation including GABA for ingestion in a drink or beverage. Each of the components is dissolved into an amount of a beverage to the appropriate concentrations indicated below. In the illustrative embodiment presented in Table 4 below, an amount of the calorie-free artificial sweetener, acesulfame potassium, also known as Ace-K, is incorporated into the formulation, along with an amount of glycerin, in order to reduce the amount of sugar necessary to obtain a desired level of sweetness. In at least one further embodiment, sucralose and/or xylitol may be utilized to provide the desired degree of sweetness. Of course, a flavor component may be added in addition to or in lieu of one or more of the sweeteners in the exemplary relaxation formulation presented below in Table 4. Once again, it is well within the scope and intent of the present invention for additional embodiments of a drink or beverage delivery system including GABA to be employed to administer the present relaxation formulation to a person.

TABLE 4

| Component | Concentration |
| --- | --- |
| Tryptophan | 1-5 grams/liter ("g/L") |
| Gamma-aminobutyric acid | 1-5 g/L |
| Malic Acid | 0.5-2.0 g/L |
| Sodium Benzoate | 0.5-1.5 g/L |
| Acesulfame potassium | 0.500-1.000 g/L |
| Sugar | 0.500-1.000 g/L |
| Glycerin | 0.5%-2.0%, by weight |

In at least one embodiment, the present relaxation formulation having approximately the following concentrations of components is incorporated into a drink or beverage: tryptophan—3.33 g/L; gamma-aminobutyric acid ("GABA")—3.33 g/L; malic acid—1.19 g/L; sodium benzoate—1.0 g/L; acesulfame potassium—0.747 g/L; sugar—0.623 g/L; and, glycerin—1%, by weight.

Table 5 below is illustrative of one embodiment of the present relaxation formulation for use in a delivery system comprising an inert vaporizable compound, to allow the active components to be inhaled directly into a person's lungs, in the manner disclosed above. Each of the components is dissolved into an amount of an inert vaporizable compound to the concentrations indicated below. Of course, it is well within the scope and intent of the present invention for additional embodiments of a vaporizable delivery system to be employed to administer the present relaxation formulation to a person.

TABLE 5

| Component | Concentration |
| --- | --- |
| Tryptophan | 1-5 mg/ml |
| Melatonin | 1-5 mg/ml |
| Gamma-aminobutyric acid | 1-5 mg/ml |

In at least one embodiment, the present relaxation formulation having approximately the following concentrations of active components is incorporated into delivery system employing an inert vaporizable compound: tryptophan—1.8 mg/ml; melatonin—1.8 mg/ml; and, gamma-aminobutyric acid—1.2 mg/ml.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described,

What is claimed is:
1. A relaxation formulation structured to induce a deep state of relaxation in a person, said relaxation formulation comprising:
   tryptophan, tyrosine, melatonin, and at least one vitamin selected from the group consisting of vitamin B3, vitamin B6, and vitamin B12,
   wherein a unit dosage of said relaxation formulation comprises:

an amount of L-tryptophan in a range of about 250 to 3,000 milligrams, an amount of tyrosine in a range of about 25 to 300 milligrams, an amount of melatonin in a range of about 1 to 10 milligrams, an amount of vitamin B3 in a range of about 3 to 36 milligrams, an amount of vitamin B6 in a range of about 5 to 75 milligrams, and an amount of vitamin B12 in a range of about 1 to 10 micrograms, and wherein said amount of tyrosine relative to said amount of L-tryptophan is in a ratio of about 10:1 of L-tryptophan:tyrosine.

2. The relaxation formulation as recited in claim 1 further comprising a delivery system.

3. The relaxation formulation as recited in claim 2 wherein said delivery system comprises a chocolate brownie having a net weight of about 2 ounces.

4. The relaxation formulation as recited in claim 2 wherein said delivery system comprises an inert vaporizable compound.

5. A method for inducing a deep state of relaxation in a person, wherein the method comprises the steps of:

administering at least a portion of a unit dosage of a relaxation formulation to the person, wherein the relaxation formulation comprises a predetermined amount of each of tryptophan, melatonin, vitamin B3, and vitamin B6, and administering at least the portion of the relaxation formulation to the person via a delivery system, wherein the delivery system comprises an aqueous sublingual spray.

* * * * *